United States Patent [19]

Tulip

[11] Patent Number: 5,748,325
[45] Date of Patent: May 5, 1998

[54] GAS DETECTOR FOR PLURAL TARGET ZONES

[76] Inventor: John Tulip, 11625 Edinboro Rd., Edmonton, Alberta, Canada, T6G 1S2

[21] Appl. No.: 526,573

[22] Filed: Sep. 11, 1995

[51] Int. Cl.$^6$ ................................................... G01N 21/61
[52] U.S. Cl. ............................................................ 356/437
[58] Field of Search ..................................... 356/437, 438

[56] References Cited

U.S. PATENT DOCUMENTS

| | | | |
|---|---|---|---|
| 3,697,185 | 10/1972 | Kassel et al. | 356/410 |
| 4,459,024 | 7/1984 | Gergely | 356/342 |
| 4,489,239 | 12/1984 | Grant et al. | 250/339 |
| 4,516,858 | 5/1985 | Gelbwachs | 356/437 |
| 4,684,258 | 8/1987 | Webster | 356/409 |
| 4,820,045 | 4/1989 | Boisde et al. | 356/319 |
| 4,934,816 | 6/1990 | Silver et al. | 356/409 |
| 5,026,991 | 6/1991 | Goldstein | 250/343 |
| 5,202,570 | 4/1993 | Tanaka et al. | 250/575 |
| 5,241,177 | 8/1993 | Albrecht | 250/338.5 |
| 5,255,073 | 10/1993 | Wallen et al. | 356/437 |
| 5,301,014 | 4/1994 | Koch | 356/437 |
| 5,339,155 | 8/1994 | Partridge et al. | 356/437 |

OTHER PUBLICATIONS

Ultrasensitive dual–beam absorption and gain spectroscopy: applications for near–infrared and visible diode laser sensors, Mark G. Allen, Karen L. Carleton, Steven J. Davis, William J. Kessler, Charles E. Otis, Daniel A. Palombo, and David M. Sonnenfroh, Applied Optics, vol. 34, No. 18, 20 Jun. 1995, pp. 3240–3248.
Abstract of U.S. Patent No. 5,448,071, issued Sep. 5, 1995, McCaul, et al, 5 pages.
Abstract of U.S. Patent No. 5,267,019, issued Nov. 30, 1993, Whittaker, et al, 2 pages.
Abstract of U.S. Patent No. 5,173,749, issued Dec. 22, 1992, Tell, et al, 2 pages.
Abstract of U.S. Patent No. 5,047,639, issued Sep. 10, 1991, Wong, 2 pages.
Abstract of U.S. Patent No. 4,968,887, issued Nov. 6, 1990, Wong, 2 pages.
Abstract of U.S. Patent No. 5,477,321, issued Dec. 19, 1995, Johnson, 2 pages.
Abstract of U.S. Patent No. 5,442,438, issued Aug. 15, 1995, Batchelder, et al, 4 pages.
Abstract of U.S. Patent No. 5,412,467, issued May 2, 1995, Malczewski, et al, 2 pages.
U.S. Navy fiber optic sensor technology, Carl P. Jacobson, SPIE vol. 3000, 0277–7B6X/97/51, pp. 1–8.
Code division multiplexing of fiber optic sensors with LED sources, Henry K. Whitesel and John K. Overby, SPIE vol. 3000, 0277–7B6X/97/pp. 9–16.
Development of a Fiber Optic Sensor Network for Naval Applications, R. Tarazona, J. Marechal–Fabre, SPIE vol. 3000, 0277–7B6X/97/pp. 17–28.
SpectraScan Open Path Monitor, Bovar Western Research, product brochure, 2 pages, believed to be dated 1997, but describes technology believed to have been on sale in the United States prior to filing of the patent application.

(List continued on next page.)

*Primary Examiner*—Richard A. Rosenberger
*Attorney, Agent, or Firm*—Anthony R. Lambert

[57] ABSTRACT

Light from a laser transmitter propagates along several optical light guides from a laser transmitter to a laser receiver. The optical light guides form a guided light path traversing each of several target zones where unwanted gas may be present. An optical switch permits selection of one of the paths and hence one of the target zones for the detection of gas. A preferred light guide uses optical fibers with optical switches, or a combination of a splitter and a switch. A lens system provides for the collection of light from a transmitting fiber optic and receiving fiber optic. The gas detector is provided with means to eliminate phase sensitivity of the detector.

9 Claims, 12 Drawing Sheets

OTHER PUBLICATIONS

Adjoint Spectrum I: an Algorithm to Extract Target Spectra Under Spectral Interferences for Use in On–Line Spectrometry, Moncef Bouzidi, Naoki Kagawa, Osami Wada and Ryuji Koga, Jpn. J. Appl. Phys. vol. 31 (1992) Pt. 3, No. 12A, pp. 4071–4080.

Effects of speckle on the range precision of a scanning lidar, Jon Y. Wang and P. Andrew Pruitt, 20 Feb. 1992/vol. 31, No. 6/Applied Optics, pp. 801–808.

Frequency modulation and wavelength modulation spectroscopies: comparison of experimental methods using a lead–salt diode laser, David S. Bomse, Alan C. Stanton, and Joel A. Silver, Applied Optics, vol. 31, No. 6, 20 Feb. 1992, pp. 718–731.

Frequency–modulation spectroscopy for trace species detection: theory and comparison among experimental methods, Joel A. Silver, Applied Optics, vol. 31, No. 6, 20 Feb. 1992, pp. 707–717.

Quantum noise–limited FM spectroscopy with a lead–salt diode laser, Clinton B. Carlisle, David E. Colper and Horst Preier, Applied Optics, vol. 28, No. 13, pp. 2567–2576.

Remote Sensing of Methane Gas by Differential Absorption Measurement Using a Wavelength Tunable DFBLD, Y. Shimose, T. Okamoto, A. Maruyama, M. Aizawa, and H. Nagai, IEEE Photonics Techndology Letters, vol. 3, No. 1, Jan., 1991, pp. 86–87.

Absorption measurement of $v_2+2v_3$ bank of $CH_4$ at 1.33 μm using an InGaAsP light emitting diode, Kinpui Chan, Hiromasa Ito, and Humio Inaba, Applied Optics, vol. 22, No. 23, 1 Dec. 1983, pp. 3802–3804.

Remote detection of methane with a 1.66–μm diode laser, Kiyoji Uehara and Hideo Tai, Applied Optics, vol. 31, No. 6, 20 Feb. 1992, pp. 809–814.

Signal recording and averaging in diode–laser spectroscopy, Kiyoji Uehara, Optics Letters, vol. 12, No. 2, Feb. 1987, pp. 81–83.

Near–infrared diode lasers monitor molecular species, David E. Cooper and Ramon U. Martinelli, Laser Focus World, Nov., 1992, 5 pages.

Diode Lasers Finding Trace Gases in the Lab and the Plant, David Bomse, Photonics Spectra, Jun., 1995, pp. 88–93.

Diode laser spectroscopy for gas monitoring of environmental pollution and for industrial process and emission control, Ase Margrete Ballangrud, A thesis submitted to the University of Oslo in partial fulfillment of the requirements for the degree Dr. Scient., Jun., 1993, 165 pages.

All–Optical–Fiber–Based Remote Sensing System for Near Infrared Absorption of Low–Level $CH_4$ Gas, Kinpui Chan, Hiromasa Ito, Humio Inaba, Journal of Lightwave Technology, vol. LT.3, No. 12, Dec., 1987, pp. 1706–1711.

Fiber Optics for Atmospheric Mine Monitoring, T.H. Dubaniewicz, J.E. Chilton, and H. Dobroski, U.S. Bureau of Mines, Pittsburgh, PA, 1991 IEEE, pp. 1243–1249.

Applications of IR–Fibers in Remote Gas–Spectroscopy, D. Pruss, P. Dreyer and E. Koch, Dragerwerk AG, Federal Republic of Germany, SPIE vol. 799 New Materials for Optical Waveguides (1987), pp. 117–122.

Long–Distance Simultaneous Detection of Methane and Acetylene by Using Diode Lasers Coupled with Optical Fibers, Hideo Tai, Kazushige Yamamoto, Masahiko Uchida, Susumu Osawa, and Kiyoji Uehara, IEEE Photonics Technology Letters, vol. 4, No. 7, Jul., 1992, pp. 804–807.

10 km–Long Fibre–Optic Remote Sensing of $CH_4$ Gas by Near Infrared Absorption, K. Chan, H. Ito, H. Inaba, T. Furuya, Applied Physics B 38, 11–15 (1985), pp. 11–15.

Evanescent Wave Methane Detection Using Optical Fibres, B. Culshaw, F. Muhammad, G. Stewart, S. Mururay, D. Pinchbeck, J. Norris, S. Cassidy, M. Wilkinson, D. Williams, I. Crisp, R. Van Ewyk and A. McGhee, Electronics Letters, 19th Nov. 1992, vol. 28, No. 24, pp. 2232–2234.

A novel optical fibre methane sensor, J.P. Dakin, C.A. Wade, D. Pinchbeck, J.S. Wykes, SPIE vol. 734 Fibre Optics '87: Fifth International Conference on Fibre Optics and Opto–Electronics (1987), pp. 254–260.

Remote Flammable Gas Sensing Using a Fluoride Fibre Evanescent Probe, V. Ruddy, B. MacCraith, S. McCabe, SPIE vol. 1267 Fiber Optic Sensors IV (1990), pp. 97–103.

Fiber Optics network for the adverse coal mining environment, Jacek K. Zientkiewicz, and Zbigniew Lach, SPIE vol. 1366 Fiber Optics Reliability: Benign and Adverse Environments IV (1990), pp. 45–56.

Measurements of cross–sensitivity to contaminant gases using a highly–selective optical–fibre–remoted methane sensor based on correlation spectroscopy, Henry O. Edwards and John P. Dakin, SPIE vol. 1587 Chemical, Biochemical, and Environmental Fiber Sensors III (1991), pp. 250–257.

In Situ and Real–Time Measurement of Methane Concentration in Rice Paddy Field at Okayama University Using Tunable Diode Laser Absorption Spectrometry, Naoki Kagawa, Osami Wada, Xu Hai, Ryuji Koga, Hiroya Sano and Kazayuki Inubushi, Jpn. J. Appl. Phys. vol. 32 (1993) Pt. 1, No. 1A, pp. 244–245.

Real Time Measurement of Methane Concentration in the Atmosphere, Y. Yamasaki, S. Takeuchi, Y. Akimoto, CPEM '88 Digest, pp. 235–236.

Remote detection of gases by diode laser spectroscopy, A. Mohebati and T.A. King, Journal of Modern Optics, 1988, vol. 35, No. 3, 319–324.

Fiber–Optic evanescent–wave methane–gas sensor using optical absorption for the 3.392–μm line of a He–Ne laser, Hideo Tai and Hiroaki Tanaka, Toshihiko Yoshino, Jun. 1987, vol.12, No. 6, Optics Letters, pp. 437–439.

Fiber Optics for Mine Gas Monitoring, T.H. Dubaniewicz and J.E. Chilton, Chapter 8, Mine Health and Safety, pp. 81–88, undated.

D–Shaped Optical Fibre Design for Methane Gas Sensing, F.A. Muhammad and G. Stewart, Electronics Letters, 18th Jun., 1992, vol. 28, No. 13, pp. 1205–1206.

A simple intrinsic optical–fibre chemical sensor, m. Archenault, H. Gagnaire, J.P. Goure and N. Jaffrezic–Renault, Sensors and Actuators, B. 8 (1992) 161–166.

GAS DETECTOR FOR PLURAL TARGET ZONES

FIELD OF THE INVENTION

This invention relates to laser absorption spectroscopy with frequency modulation detection, and in particular to the remote detection of gases using laser absorption spectroscopy.

BACKGROUND OF THE INVENTION

In laser absorption spectroscopy with frequency modulation detection, a laser diode is current modulated at a high frequency. This results in the optical frequency of the laser being modulated at the same frequency as the current. It also causes light amplitude modulation at the same frequency. The frequency modulated light is emitted from the laser diode, passed through a target zone, which may or may not contain a gas or gases of interest and received at a detector, which contains a photo detector. The gas or gases of interest will have an absorption spectrum containing one or more lines or frequency bands in which light of that frequency is absorbed.

As the laser light frequency scans across the gas absorption lines, the absorption varies. The challenge in the art is to see the small amplitude change in light level caused by gas absorption as the laser wavelength is scanned across the gas line above the amplitude variations caused by the laser diode.

The method depends upon the nonlinear absorption change as the laser line scans across the Lorentzian absorption line. In one conventional method, harmonics of the modulation frequency are measured. The photo detector circuit will see second third, fourth, etc. harmonics of the laser modulation frequency caused by the nonlinear gas absorption. Laser amplitude modulation is dominated by the fundamental modulation frequency so it does not swamp out the relatively weak harmonics. In another conventional method, the laser is modulated at two frequencies, which is referred to as the "two tone method." Nonlinear absorption will mix these frequencies so the photodetector sees a frequency component, which is the difference between the two frequency components.

Common to all of these techniques is that the detecting circuit must select a particular frequency component and reject the rest. This is known as homodyne detection. In the art, this is done by taking a local oscillator at the required frequency and mixing it with the detected signal. The mixer will generate a d.c. or low frequency output, which is easy to isolate using a low pass filter. A detected signal containing frequency components $w_0$, $w_1$, $w_2$, $w_3$, etc is mixed with frequency component $w_0$, which is taken directly from the current modulator for the laser diode. The dc output ($w_0$-$w_0$) from the mixer is isolated with a low pass filter and the level of this signal provides an indication of the presence of a target gas in the target zone.

It is also known to simultaneously modulate the diode current at a relatively low frequency using a ramp. This ramp has a relatively large amplitude so it will scan the laser frequency through the absorption line. In this way it is not necessary to control the laser frequency so that it exactly coincides with the gas absorption line, which is difficult. The detected high frequency signal under these conditions is not at a d.c. frequency, but is modulated as the laser scans across the absorption line. This results in the well known "W" shaped detected waveforms.

In the art the required local oscillator is generated by taking the laser modulation signal and modifying it to give the desired local oscillator, as for example shown in Koch, U.S. Pat. No. 5,301,014, in which the second harmonic signal is detected. In this case the local oscillator is formed by taking the diode/laser modulator signal and passing it through a frequency doubling circuit. As a result the local oscillator has fixed amplitude and phase.

The use of a mixer to detect a chosen frequency is sensitive to phase. The mixed output is maximum when the signal and local oscillator are in phase and zero when they are 90° out of phase. This is referred to as phase sensitive detection. This method is preferred because it results in high signal to noise ratio. The electrical random noise passing through a filter is proportional to the square root of the bandwidth so that a small bandwidth filter results in a low noise level. If the filter is tuned to the signal, it will have minimal effect upon the signal so that a narrow bandwidth filter will provide a high signal to noise ratio. It is, however, difficult to construct electrical filters with a high Q-value, which is the ratio of the signal frequency and bandwidth. However the mixing circuit used in phase sensitive detection shifts the signal frequency to a low value close to d.c. In this case it is possible to use a relatively low Q low pass filter and obtain a small bandwidth and random noise throughput.

Since phase sensitive detection depends upon the relative phases of the signal and local oscillator, these phases must be adjusted and then maintained. For fixed path length applications the phase of the signal is constant so that adjustment is usually performed using a phase shifting circuit in the local oscillator.

SUMMARY OF THE INVENTION

For remote applications of the gas detector, it is desirable to make operation of the gas detector as simple as possible. The inventor has identified that this can be achieved by ensuring that the local oscillator used for homodyne detection of the detected signal is always in phase with the detected signal. In one aspect of the invention, therefore, the detected signal is used as a source for the local oscillator.

In addition, the laser construction is complicated by the fact that it is likely to be used in hazardous environments, with the result that the package becomes quite expensive. The inventor has therefore proposed a system in which light from a laser transmitter propagates along several optical light guides from a laser transmitter to a laser receiver. The optical light guides form a guided light path traversing each of several target zones where unwanted gas may be present. An optical switch permits selection of one of the paths and hence one of the target zones for the detection of gas. A preferred light guide uses optical fibers with optical switches, or a combination of a splitter and a switch.

A particular arrangement for the collection of light from a transmitting fiber optic and receiving fiber optic is also provided.

In addition, in cases where the laser receiver and detection system is sensitive to phase, adjustment of several light paths for phase becomes difficult, and therefore in one aspect of the invention, the gas detector is provided with means to eliminate phase sensitivity of the detector.

According to further aspect of the invention, a remote laser head is coupled in each guide light path between the laser transmitter and the laser receiver. The remote laser head, in use, is installed at a target zone remote from the laser transmitter and laser receiver.

A gas reference cell is also preferably provided on a guided light path between the laser transmitter and laser receiver. Sequential switching between the remote laser heads and the gas reference cell permits automatic calibration of each of the multiple guided light paths.

These and other aspects of the invention are described in the detailed description and claimed in the claims that follow.

BRIEF DESCRIPTION OF THE DRAWINGS

There will now be described preferred embodiments of the invention, with reference to the drawings, by way of illustration, in which like numerals denote like elements and in which.

DETAILED DESCRIPTION OF PREFERRED EMBODIMENTS

Figure 1:
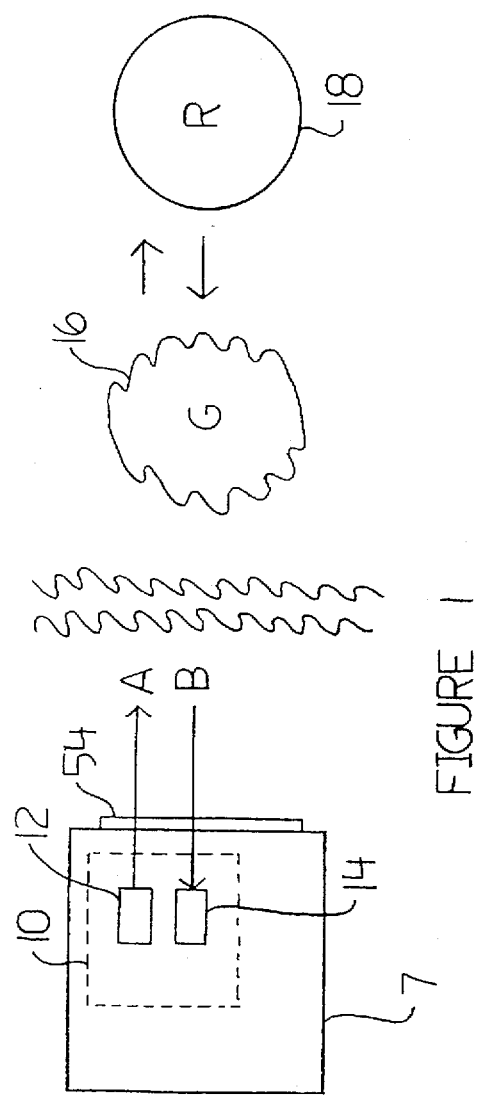
FIG. 1 shows an overall schematic of a gas detector, target zone and reflector.

Referring to FIG. 1, an exemplary gas detector 10 includes a laser transmitter 12 and laser receiver 14. Typically, in use, light from the laser transmitter 12 is directed towards gas in a target zone 16, reflected from a reflector 18, and received back at the laser receiver 14. The distance from laser transmitter 12 to laser receiver 14 may be more than 200 meters, and may be an oil or gas installation. Target gases include hydrogen fluoride, hydrogen sulphide, ammonia, water, hydrogen chloride, hydrogen bromide, hydrogen cyanide, carbon monoxide, nitric oxide, nitrogen dioxide, oxygen and acetylene, although a major expected use of the invention is for the detection of methane.

The laser transmitter 12 preferably uses a tunable diode laser to produce frequency modulated light output including light having a wavelength that is absorbed by the target gas. Such tunable diode lasers are well known in the art in which an injection current is modulated to produce frequency modulated output. Since it is difficult to ensure that the carrier frequency of light from the laser is at an absorption line of the target gas, the carrier frequency is preferably tuned through the absorption line with a ramp. Typically, therefore the light from the laser is modulated with a first modulation frequency corresponding to the frequency of the modulating current and a second modulation frequency corresponding to the ramp frequency. In two-tone modulation, the light from the laser will be modulated with a third modulation frequency. The light absorbed by the gas may be the carrier frequency or one of the sidebands caused by the modulation.

Figure 2:
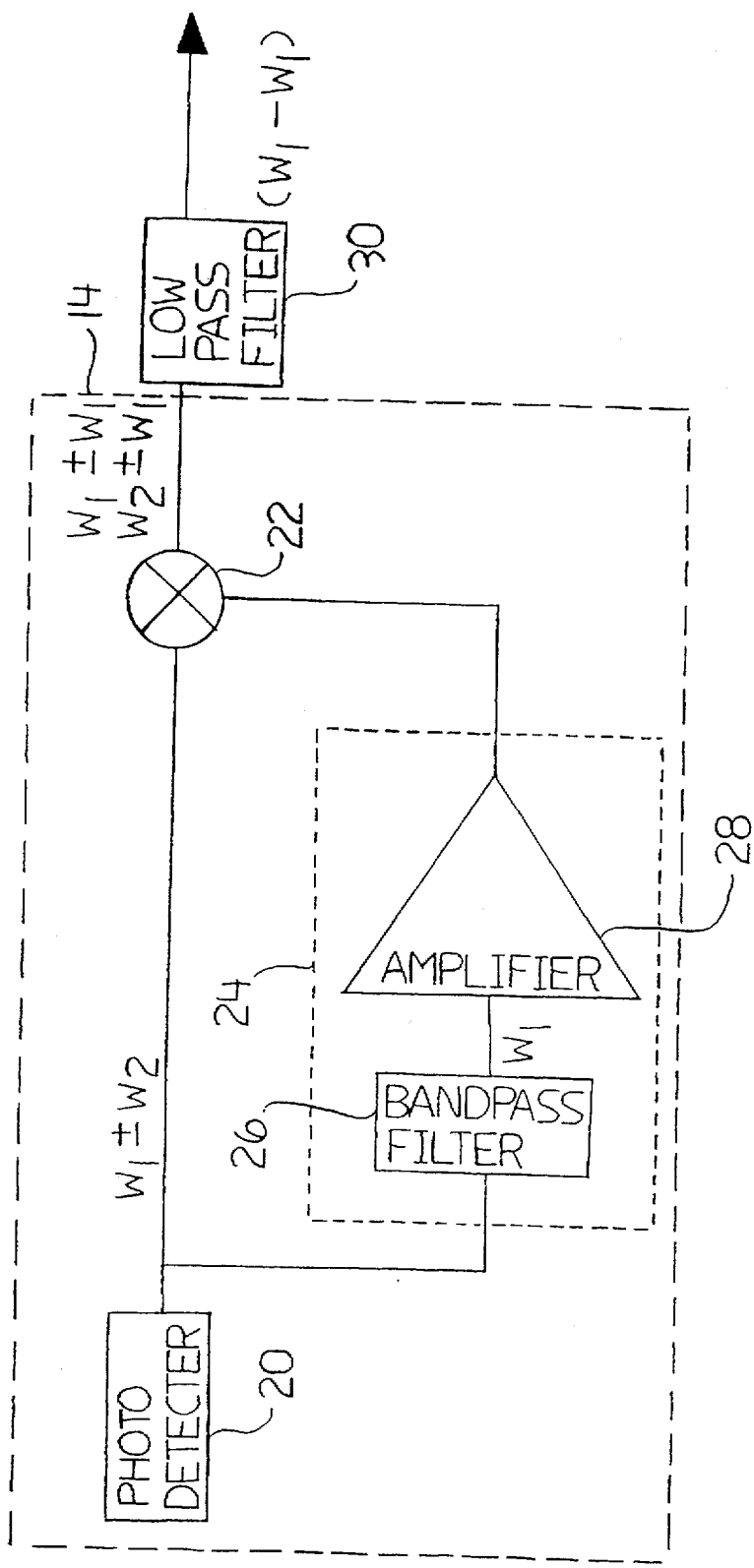
FIG. 2 is a schematic showing a first detection circuit.

While the laser receiver 12, modulation technique and laser frequency selection are all known in the art, the laser receiver 14 is new. An exemplary laser receiver 14 is shown in FIG. 2. Light from the laser that has passed through the target zone is detected by photo detector 20, converted to an electrical signal and passed to mixer 22. The detected signal will contain many frequencies $w_1$, $w_2$, corresponding to the modulation frequencies of the light emitted from the laser and their harmonics. The signal from the photo detector 20 is also passed to reference signal generator 24, where the signal is bandpass filtered in filter 26 to isolate one of the frequencies, for example $w_1$, and then amplified in amplifier 28 to produce a reference signal. The reference signal is supplied as one of the inputs to the mixer 22 where it is mixed with the detected signal coming direct from the photo detector 20. Output from the mixer 22 is low pass filtered in filter 30 and then analyzed, for example using data analyzer 32 shown in FIG. 6. The output from low pass filter 30 will show gas absorption if the target gas is present. Analyzer 32 performs such functions as signal averaging and also preferably includes some conventional means of displaying the detected signal.

Reference signal generator 24 may also develop its reference signal from a second photo detector (not shown) although it is preferred to use one photo detector. The reference signal generator 24 generates a local oscillator $w_1$, which is independent of the laser modulation circuitry. The local oscillator always has a fixed phase relationship with the photodetector signal so that this circuit is independent of the absorption path length.

Figure 3:
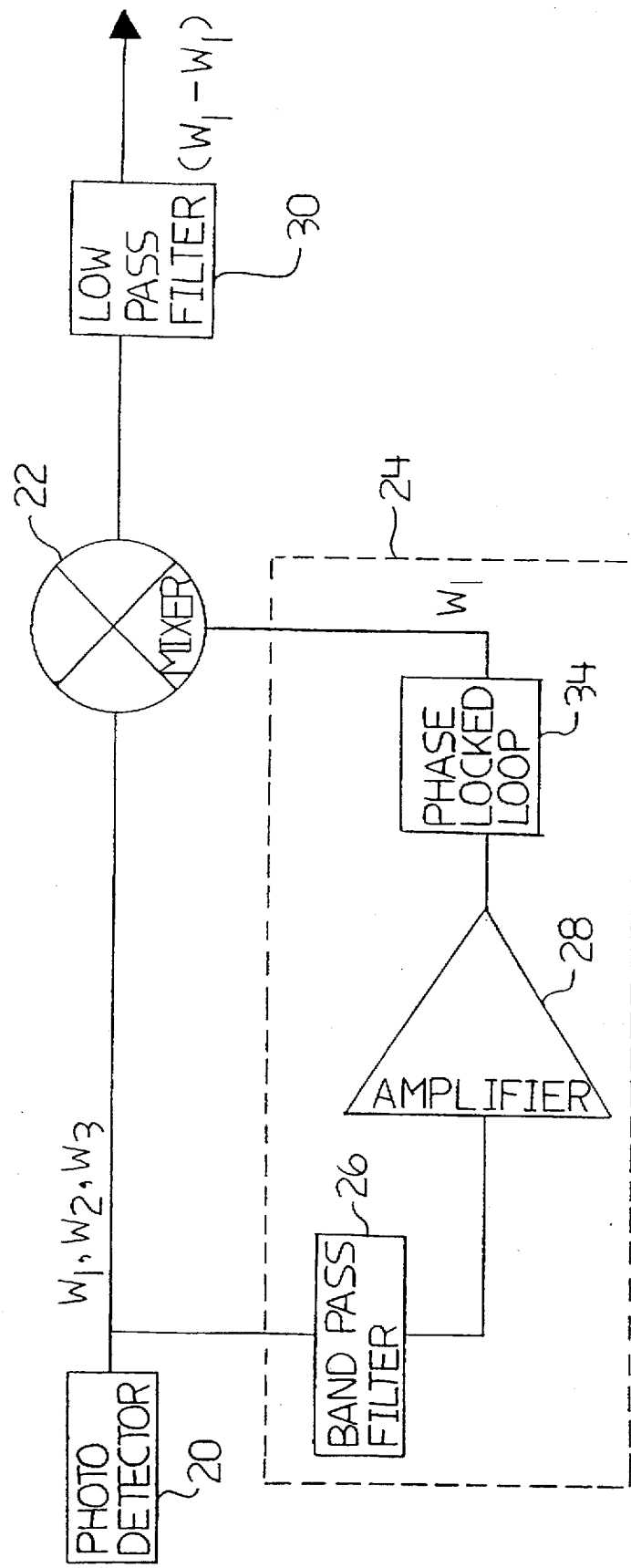
FIG. 3 is a schematic showing a second detection circuit.

A further exemplary embodiment of this invention is shown in FIG. 3. The reference signal generator 24 of FIG. 3 differs from the reference signal generator 24 of FIG. 2 by including a phase lock loop 34. The signal $w_1$ from the amplifier 28 is used to activate the phase locked loop 34 (PLL) and the output of this PLL is used as in FIG. 2 as a local oscillator. The output of the PLL 34 has the same frequency and phase as the input signal $w_1$. However, it is free from other frequencies, which can pass through the bandpass $w$, filter, such as the electrical noise over the filter bandwidth. The use of a PLL for a local oscillator consequently results in better signal-to-noise ratio in the mixer output.

Figure 4:
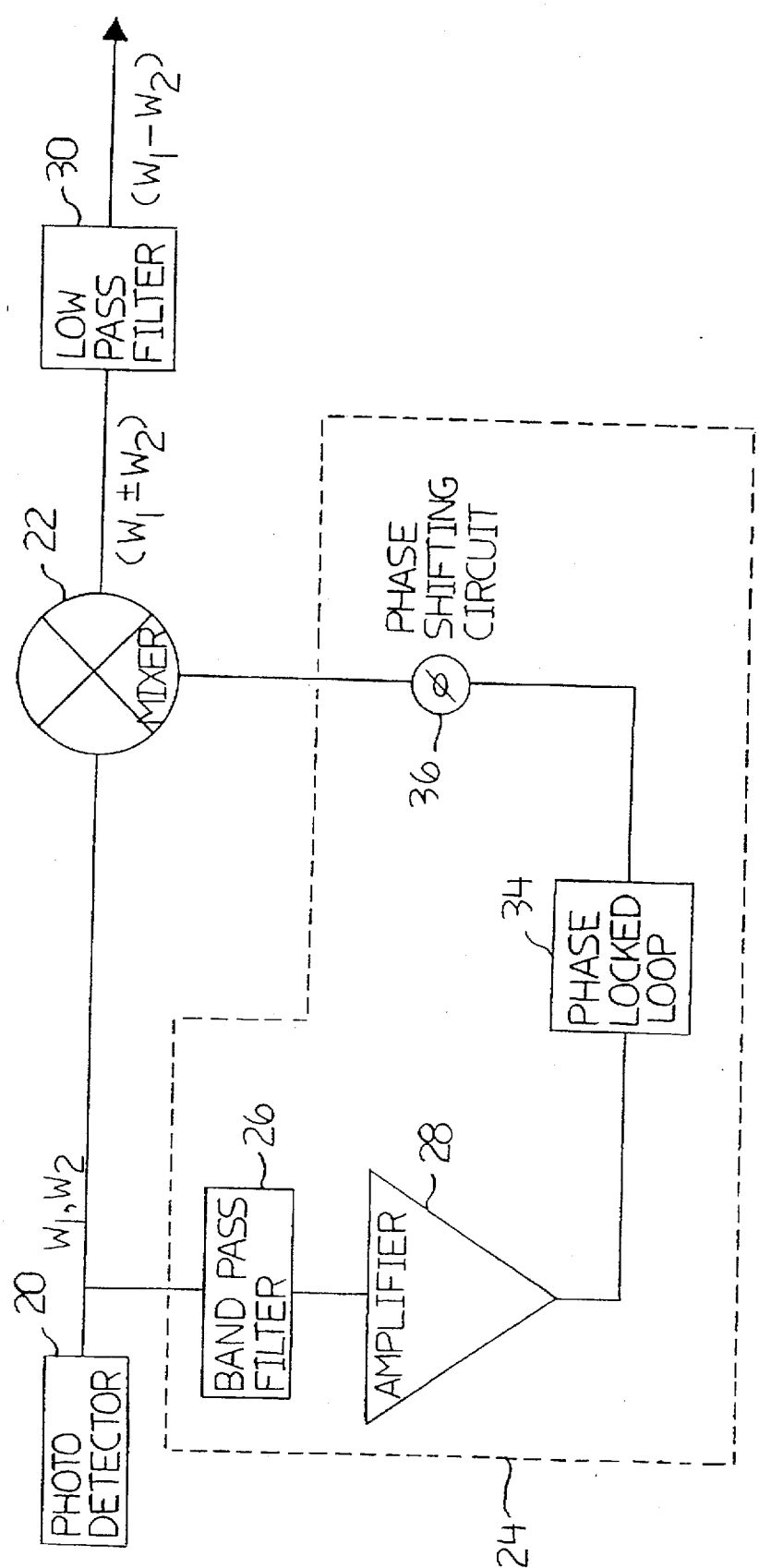
FIG. 4 is a schematic showing a third detection circuit.

A further exemplary and improved embodiment of this invention is shown in FIG. 4. In this embodiment a phase shifting circuit 36 is added to the reference signal generator 24 of FIG. 2. The phase shifting circuit 36 permits changes in the phase relationship between the signal $w_1$ and the local oscillator. The noise level in a laser absorption spectrometer may be reduced by careful phase adjustment of the reference signal generator 24 in accordance with known techniques.

Figure 5:
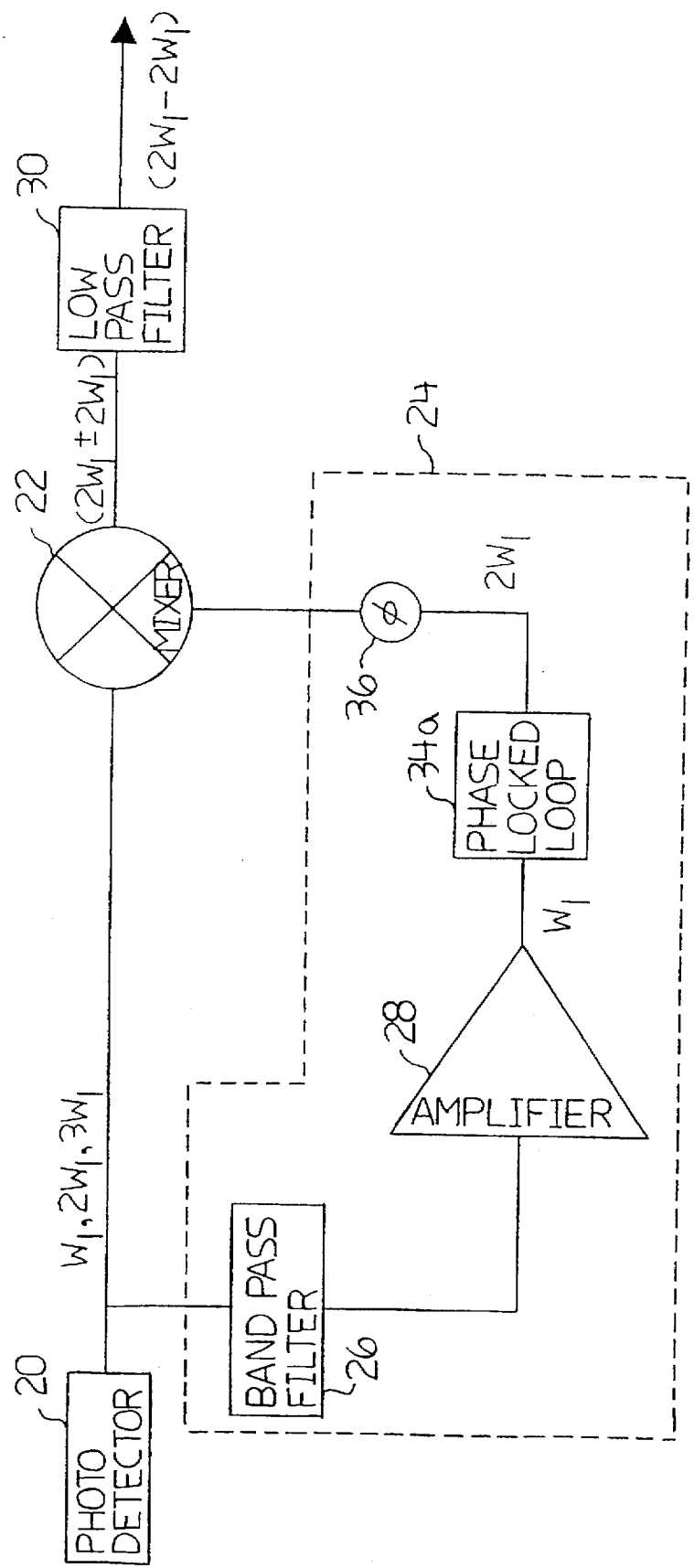
FIG. 5 is a schematic showing a fourth detection circuit.

A further exemplary and improved embodiment is shown in FIG. 5. In the embodiment of FIG. 4, the signal at the desired frequency is used to activate a phase locked loop 34. For remote application it is common for this photodetector signal to be too weak to activate the PLL 34. In the embodiment of FIG. 4, the PLL 34 is activated by a signal with a fundamental frequency, which is always stronger than the detected signal. For the absorption measurement technique in which the laser is modulated at a single frequency, the detected signal is commonly the second harmonic $2w_1$.

Figure 5A:
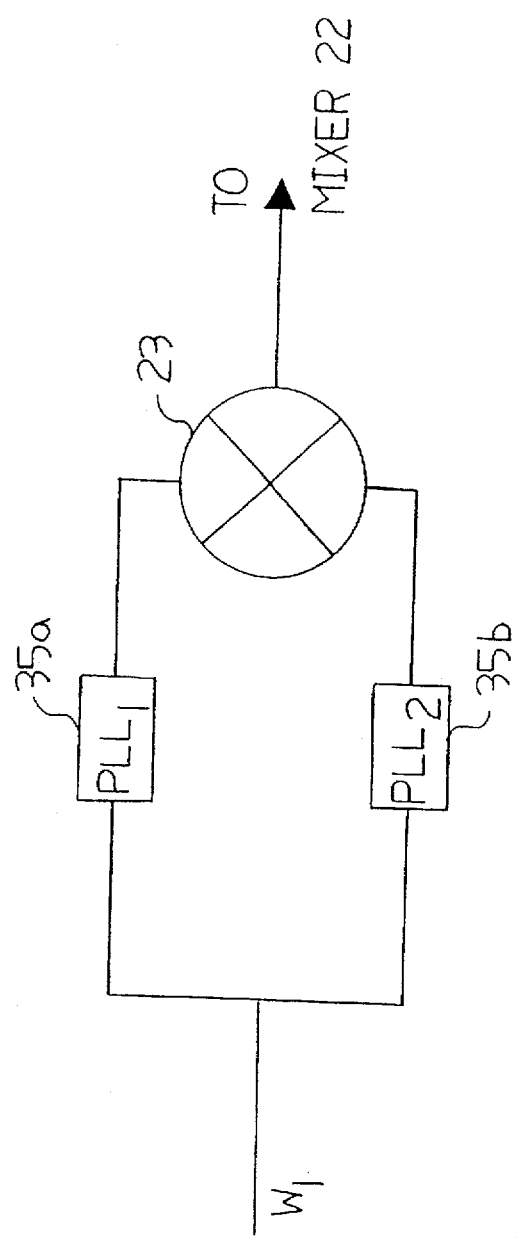
FIG. 5A is a schematic of part of an alternative reference signal generator for the embodiment of FIG. 5.
Figure 7:
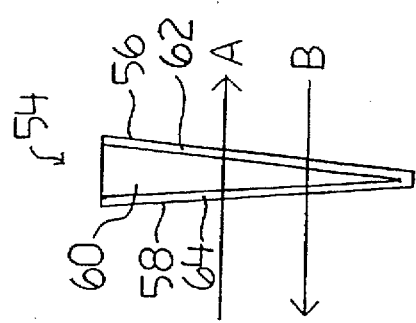
FIG. 7 is a schematic showing a section through a window for use in reducing etalon fringes in the operation of the invention.

For the technique referred to as two tone modulation the laser is modulated at two frequencies $w_1$ and $w_2$ (besides the ramp frequency) and the difference signal at frequency ($w_1 - w_2$) is detected. In FIG. 5, the PLL 35 is activated at frequency w, and generates an output at the harmonic frequency $2w_1$. This harmonic signal then acts as the local oscillator in the mixer 22 and the $2w_1$ signal is detected as desired. In this way the PLL 35, is activated by the much stronger $w_1$ signal. For two tone modulation two PLLs 35a and 35b generating $w_1$ and $w_2$ are necessary as shown in FIG. 5A. These are then combined in a secondary mixer 23 to generate a ($w_1 - w_2$) signal, which is then used as the local oscillator in the detecting circuit and input to the mixer 22.

In the method of laser absorption spectroscopy the detected signal is proportional to the quantity of gas in the absorption path length. The detected signal can hence be used as a measure of gas concentration if the path length of absorption is known. For example, light from a laser absorption spectrometer may be reflected from a distant object or reflector, as for example reflector 18 shown in FIG. 1. Light returning to the spectrometer will sense the presence of gas if the laser line coincides with the gas absorption wavelength. An estimation of the path length of light through the gas cloud will then permit an estimation of the gas concentration. To be useful the spectrometer must be calibrated so that readings of gas concentration do not change because of instrument or environmental changes. In practice, this is very difficult to achieve. Small changes in laser temperature will cause the laser wavelength to move away from the gas absorption line because laser diode wavelength is very sensitive to temperature. Environmental changes of temperature between −40° C. to +50° C., as required by industrial equipment, can also cause changes in the electronic sensitivity. It is known to use a methane cell together with feedback circuitry to regulate the laser wavelength onto the methane absorption line, in which the main limitation to sensitivity is temperature induced changes. In this invention the effects of temperature changes are minimized using a gas reference cell in a manner quite different from that previously known.

The gas cell is not used to stabilize the laser wavelength as in the prior art. In the present invention, the laser wavelength is preferably scanned using a low frequency ramp diode laser current modulation. In this way small wavelength changes caused by environmental changes to the thermoelectric temperature controlling circuit are not important. If the laser line scans through the absorption line, small offsets in the average laser wavelength are not important. This method of ramping itself is well known in the art.

Figure 6:
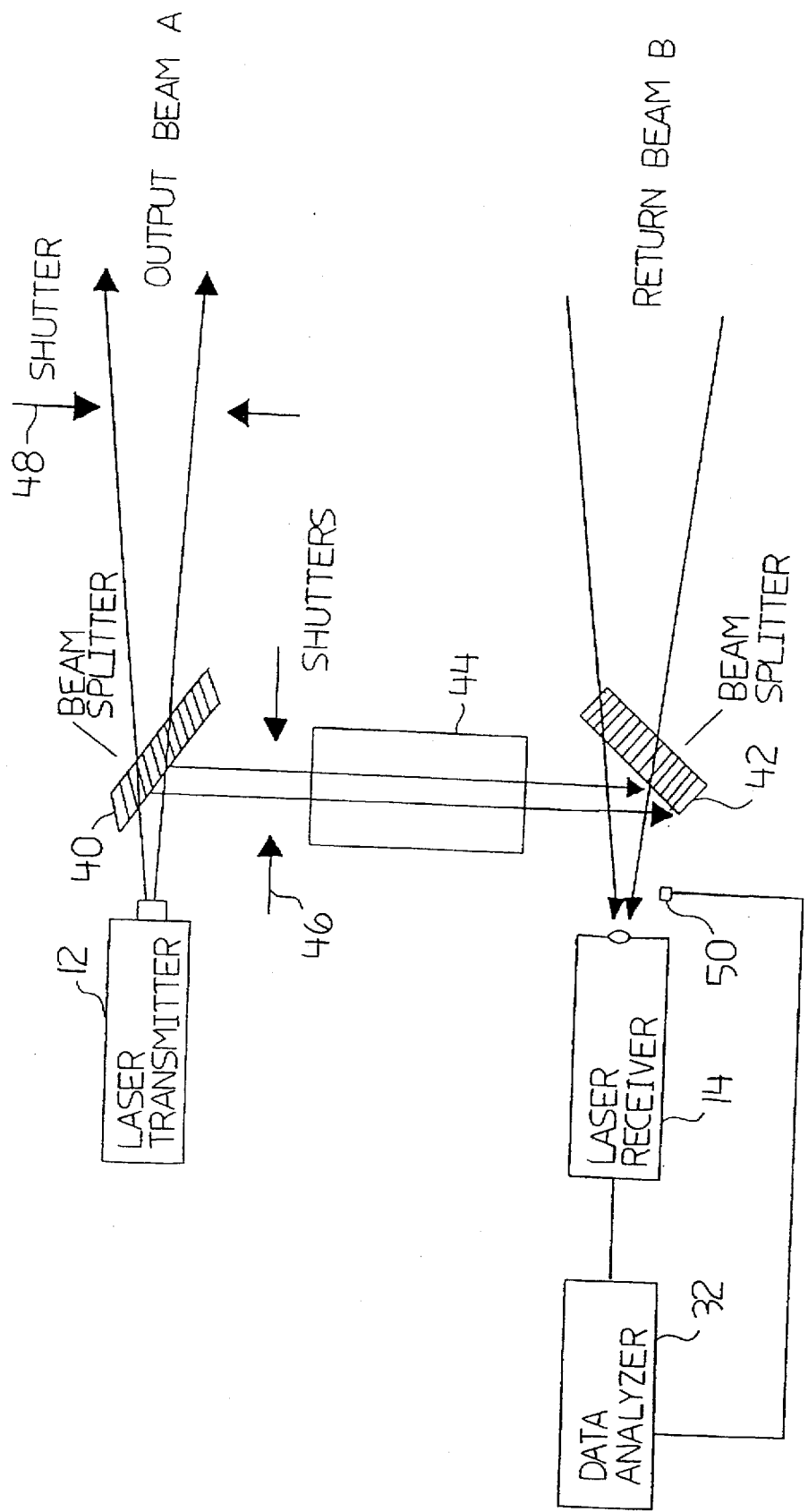
FIG. 6 is a schematic showing a gas detector used for the resolution of gas density.

A novel application of a gas reference cell is shown in FIG. 6. Part of the outgoing beam from laser transmitter 12 is reflected from beam splitters 40 and 42 into the laser receiver 14 through a small cell 44 containing the gas of interest. The main beam A is transmitted to the remote reflector 18 and the reflected beam B is also collated by the laser receiver 14 as is normal.

A first shutter system 46 is disposed on the light path from the beam splitter 40 to beam splitter 42 through the reference cell 44. A second shutter system 48 is disposed on the light path from the beam splitter 40 the beam splitter 42 that passes through a target zone to the reflector 18. Operation of the shutters 46 and 48 will expose the receiver to light in an alternating way from either the remote reflector 18 or from the gas reference cell 44. The data analyzer 32 attached to the receiver 14 output records and compares the signal from both sources for example using a Kalman filter. The use of Kalman filters and like digital processing methods for the comparison of one reference signal with a noisy signal is well known and need not be further described. Since the gas density within the reference cell 44 is known, it is possible to calculate the gas density in the path to the remote reflector 18 from a comparison of the intensity of detected light that has passed through the target zone with the intensity of light that has passed through the gas reference cell. Detecting the reference signal and then the signal from the target sequentially may be carried out several times per second or as low as several times per hour, but the duration of transmission of laser light is preferably kept to a minimum, to fractions of a second, to avoid potential damage to the eyes of those who may be nearby. This technique has several advantages.

Effects of instrument changes and environmental changes are cancelled because the changes apply equally to the remote signal and the reference signal. This system is in effect an automatic calibration. Further, for detection of hazardous gases, it is important that equipment failure is not interpreted as the absence of gas. This is referred to as a false negative signal. The sharing of the reference and remote signals within the system avoids this problem to the extent that the remote laser beam is not obstructed. For fail safe operation with this system, it is hence necessary to make use of a light level sensor 50 to ensure the presence of a return laser beam. The use of the gas reference cell requires a known phase relationship for both the reference and remote signals. It is hence not possible to simply adjust the phase of the local oscillator. Hence it is preferable to use the method shown in FIGS. 2 to 5 to avoid phase adjustment for both reference and remote signals.

In practice, the return signal to the laser receiver is not in phase with the local oscillator, which would provide the highest output signal. The phase of the signal and local oscillator are typically 10° to 40° different. This is necessary to null the noise caused by laser diode amplitude modulation. Drift in this phase difference caused by instrument and environment changes can cause significant increase in laser noise and degradation of the spectrometer sensitivity. However in the presence of a signal, adjustment of the phase to minimize noise is not possible because the signal also depends upon phase. This problem may be solved by tuning the laser wavelength away from the gas absorption line so that the signal is reduced to zero. The noise may then be reduced to a minimum by phase adjustment and then the laser line is returned onto the absorption line. Phase adjustment may be achieved with a phase shifter 36 in the reference signal generator 24. However, since it is necessary only to change the phase difference between detected and reference signals, the phase shifter 36 may be on the line carrying the detected signal. These steps may all be undertaken with the spectrometer control circuits. Consequently, the gas reference cell may be used to calibrate the remote signal automatically and also to adjust the phase of the local oscillator for minimum noise ensuring reliable fail safe operation of the device over time and in different environmental conditions.

Laser absorption spectrometers are suitable for detecting explosive gases such as methane. However the use of electrical devices in hazardous environments is highly regulated and usually requires that the equipment is mounted in explosive proof enclosures, such as enclosure 52 shown in FIG. 1. The design of explosion proof enclosures 52 is well known in the art and requires a thick window 54 through which the outgoing and return laser beam may pass. As is well known in the art, windows will behave like Fabry-Perot resonators and cause interference fringes known as etalon fringes. This effect causes wavelength dependent transmission variation, which competes with the gas absorption and causes serious reductions in signal to noise ratio and hence system sensitivity to gas. In particular, thick windows will cause fringes, which are particularly detrimental. The inventor has found that the use of a thick window with low fringe noise on an explosive proof chamber is possible if the front and back faces 56 and 58 respectively of the window 54 are at a sufficient angle to each other to move the fringes to a frequency that can be discriminated from the detected signal. The etalon fringes may then be filtered out from the detected signal using the low pass filter 30. If the window 54 is made of a laminate, the wedge shape of the window 54 may be accomplished by introducing a small wedge 60 between the two laminates 62 and 64 forming the window 54. The wedge causes the frequency difference between fringe maxima to be reduced.

When the laser wavelength scans the wedged window, it will pass through several fringes and the fringe noise recorded by the laser receiver circuit will be of relatively high frequency. The low pass filter used after the mixing circuit will hence remove this source of noise and the fringe noise will not degrade the spectrometer sensitivity.

The inventor has also discovered that operation of the invention over distances greater than 200 meters is possible if the light transmitted to a reflector on the opposite side of the target zone follows the same return path. In this manner, deviation of the light path is the same on the outgoing and returning light path and the return beam ends up back at the laser receiver, which is conveniently housed with the laser transmitter.

The reflector should be large enough to efficiently reflect the thermally deflected and refracted laser beam, and the light collector on the laser spectrometer should be large enough to collect the refracted laser beam. The reflector should be a good quality retroreflector since displacement of the return beam upon reflection tends to make the return beam follow a slightly different path. In addition, it is preferable to use as wide a laser beam as is practical.

Although detection of methane may be carried out at the commonly used 1.66 µm methane absorption band, where the absorption is fairly strong and the signal is not affected by water vapour absorption, it is preferred to carry out transmission and reception at the 1.3165 µm absorption line for methane, within the water vapour window between 1.3162 to 1.3169 µm. Since there is also an ammonia absorption line at about 1.3165 µm, if ammonia may be present, detection should also take place at about 1.3177 µm within the 1.3173 µm to 1.3184 µm water vapour band since ammonia also has an absorption line at about 1.3177 µm while methane does not. Hence, during processing of the detected signal reflected back from a reflector, detection of absorption at 1.3177 µm distinguishes ammonia from methane, and absence of detection of absorption at 1.3177 µm distinguishes methane from ammonia. The methane absorption line at 1.3165 µm is an unlikely candidate for practical measurement of methane presence since the absorption at this line is about 20 times weaker than at the conventional 1.66 µm line. However, adoption of this line for detection allows communication band lasers at about 1.32 µm to be used for both the detection of methane and ammonia.

Figure 8:
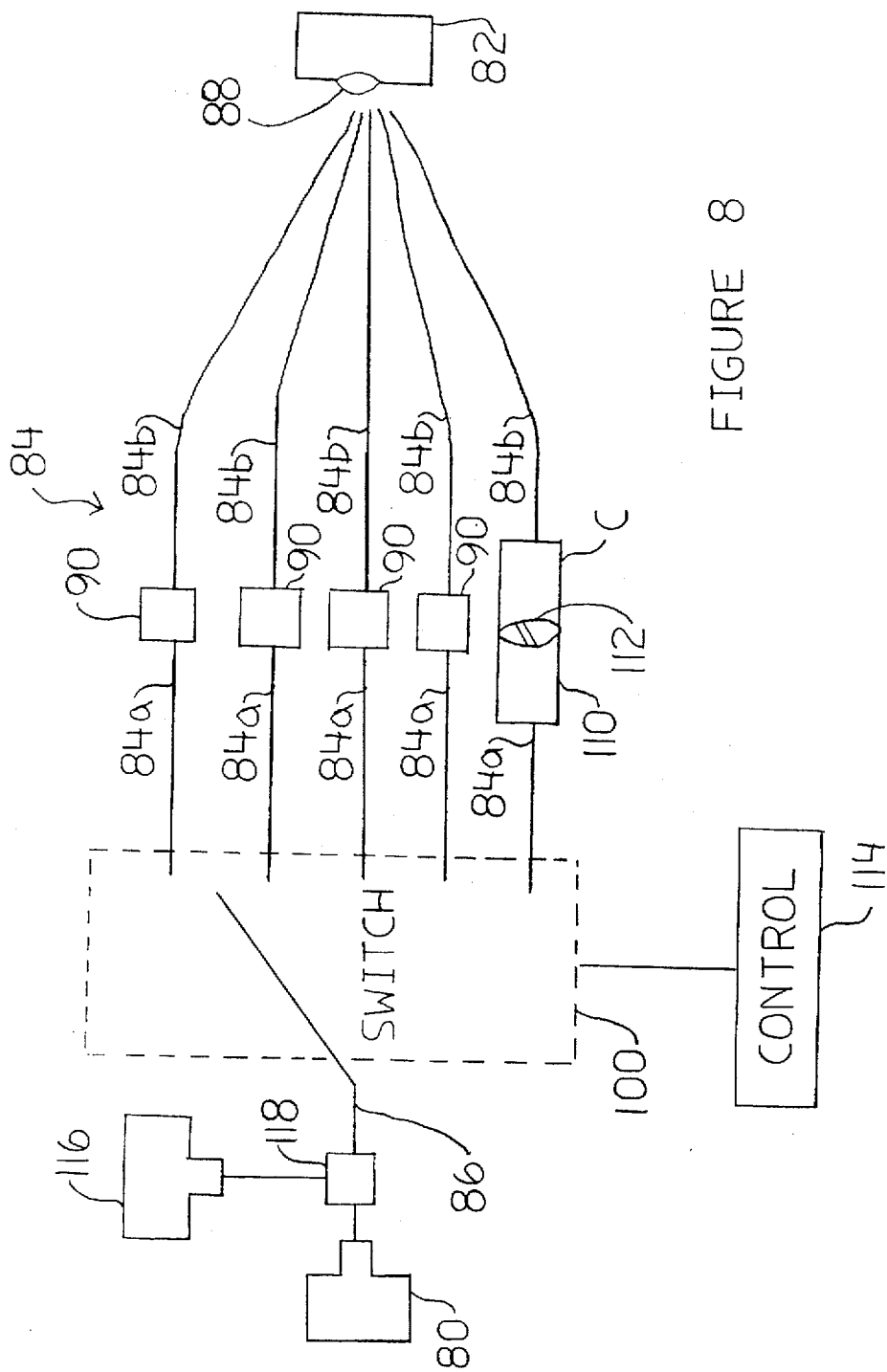
FIG. 8 is a schematic showing an embodiment of the invention with plural optical light guides traversing several distinct target zones and a gas reference cell.
Figure 11:
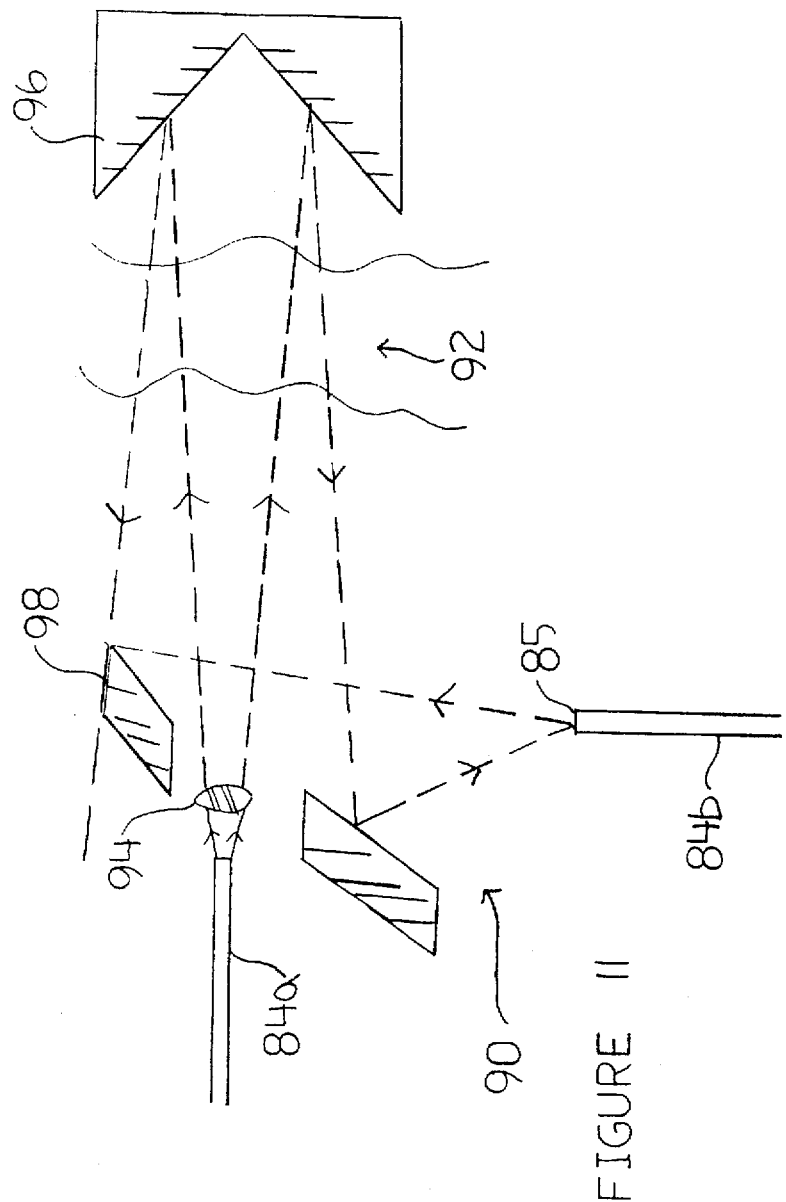
FIG. 11 is a schematic of a light guide configuration at a target zone.

Referring now to FIG. 8, a laser transmitter 80 and laser receiver 82 are shown with plural optical light guides 84 extending between them. The laser transmitter 80 is preferably but not necessarily a laser transmitter of the tunable diode type described above, and the laser receiver 82 is preferably but not necessarily made in accordance with the description of the laser receiver shown in FIGS. 2–5, including the above described system for eliminating phase sensitivity of the receiver. Each optical light guide 84 preferably is formed of a transmitting optical fiber 84a and a receiving optical fiber 84b. The transmitting optical fibers 84a are positioned to receive light from the laser transmitter 80, as for example through optical fiber, 86 and terminate at a remote laser head 90 at a target zone as shown in FIG. 11. The receiving optical fibers 84b are positioned to output light to the laser receiver 82, as for example through lens 88 or like optical element, and each has an end 85 terminating at the remote laser head 90 at a target zone 92 to receive light from one of the optical fibers 84a, the light having passed across the target zone 92.

Each laser head 90 includes a collimating lens 94 spaced from the terminus of one of the optical fiber 84a to receive and collimate light exiting the optical fiber 84a. The collimated light is directed onto a corner cube reflector 96 spaced from the collimating lens 94 at the opposite side of the target zone 92, the target zone thus being between the laser head 90 and the reflector 96. Light reflecting from the corner cube reflector 96 is collected and focused by an offset parabolic reflector 98 onto an end 85 of one of the optical fibers 84b. Conveniently, the parabolic reflector 98 includes a central aperture to permit passage of light from the optical fiber 84a through the parabolic reflector 98. The lens 94 and reflector 98 together form an exemplary optical means to direct light from optical fiber 84a through the target zone to the optical fiber 84b.

In an installation, for example at an oil industry installation, a laser head will be installed in each target zone in the installation that is to be monitored. There may be for example 30 target zones. An exemplary target zone might be a control room. With the optical fiber coupled laser head described, the laser transmitter and laser receiver may be in a location remote from each target zone, hundreds of meters away or more.

Each pair of optical fibers 84a and 84b and the corresponding laser head 90 together form a distinct guided light path from the laser transmitter 80 to the laser receiver 82 that traverses the target zone 92. The optical fibers 84a and 84b are preferably single mode fibers.

As shown in the embodiment of FIG. 8, an optical switch 100 is provided at the laser transmitter 80 to select one of the optical light guides 84. Selection of one of the optical light guides 84 connects one of the optical fibers 84a to the optical fiber 86 to complete a guided light path between the laser transmitter 80 and the laser receiver 82 for the detection of gas in the target zone traversed by the selected one of the optical light guides. The selection may be computer controlled. Fiber optic switches of this type are well known in the art and need not be further described. The optical fibers 84b guide the light from the remote laser heads 90 to optics at the laser receiver 82.

Figure 10:
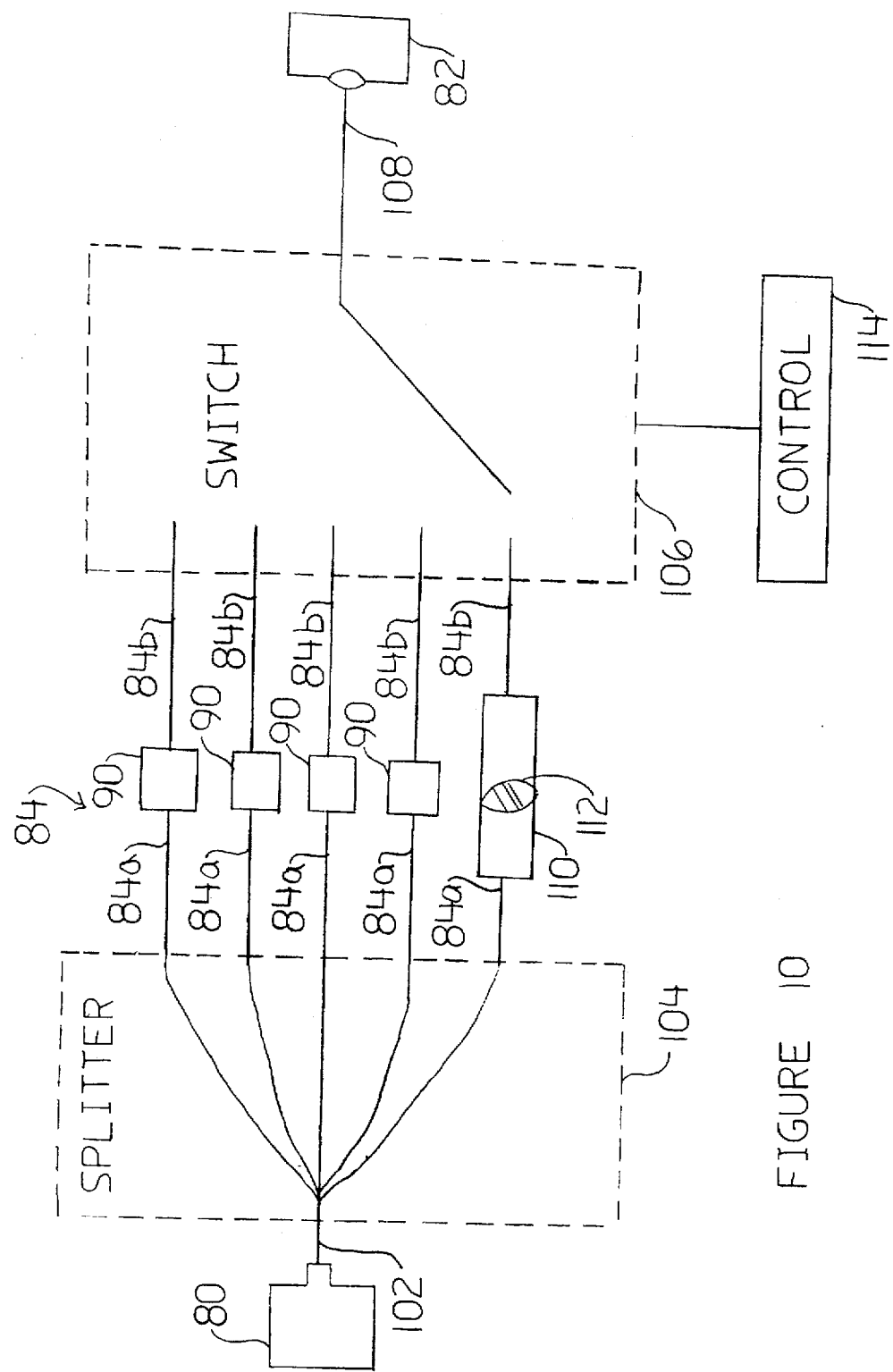
FIG. 10 is a schematic showing a second embodiment of the invention with plural optical light guides traversing several distinct target zones and a gas reference cell.

An alternative switching system is shown in FIG. 10. In this case, light from the laser transmitter 80 is guided by optical fiber 102 to a beam splitter 104 where it is split into optical fibers 84a and guided to remote laser heads 90. Light from the remote laser heads 90 is carried by optical fibers 84b to a fiber optic switch 106 similar to switch 100, except that switch 106 may be multi-mode. Switch 106 is connected to laser receiver 82 through optical fiber 108. Setting of the switch 106 selects one of the guided light paths 84 defined by the optical fibers 84a, 84b and the optics in the laser head 90, and connects one of the optical fibers 84b to the optical fiber 108 to complete a guided light path between the laser transmitter 80 and the laser receiver 82 for the detection of gas in the target zone traversed by the selected one of the optical light guides.

Figure 9:
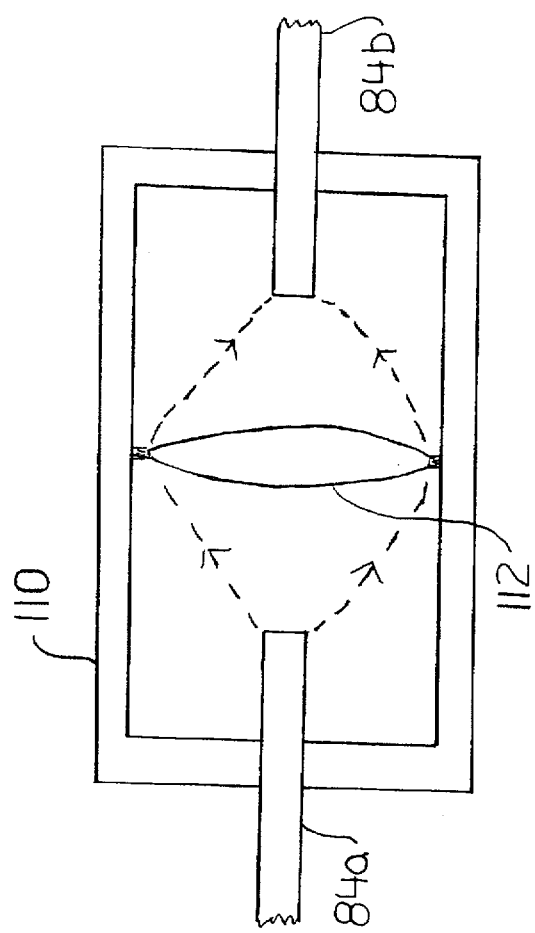
FIG. 9 is a schematic of a gas reference cell for use in the embodiment of the invention shown in FIG. 8.

For the remote detection of gas from plural zones, it is preferable to locate a gas reference cell 110 in a guided light path selectable by the switch 100 or 106. Hence, for measurement of gas density, the light from the laser transmitter 80 can be selectively directed through one of the remote laser heads 90 or the gas reference cell 110. For use with an optical fiber, it is preferred that a refocusing lens 112 be provided in the gas reference cell 110, as shown in FIG. 9, to collimate light from the optical fiber 84a and focus it onto optical fiber 84b. Other methods of focusing the light onto the fiber 84b could be used.

A control 114, which may be part of the data analyzer 32 shown in FIG. 6, may be used to sequentially select one of the remote laser heads for gas detection. In an industrial environment, the sequential switching between laser heads provides continuous repeated monitoring of several areas or zones within the environment. In addition, sequential switching between the remote laser heads 90 and the gas reference cell 110 permits automatic calibration of each of the multiple guided light paths.

For the detection of more than one gas, a second laser transmitter 116 may be connected to the optical light guides 84 through a combiner 118. The second laser transmitter 116 may operate in a narrow band separate from the band of the laser transmitter 80 and thus be used to detect a different gas species. Either one of the laser transmitters 80 and 116 may be operated sequentially, or alternately as desired.

Figure 12:
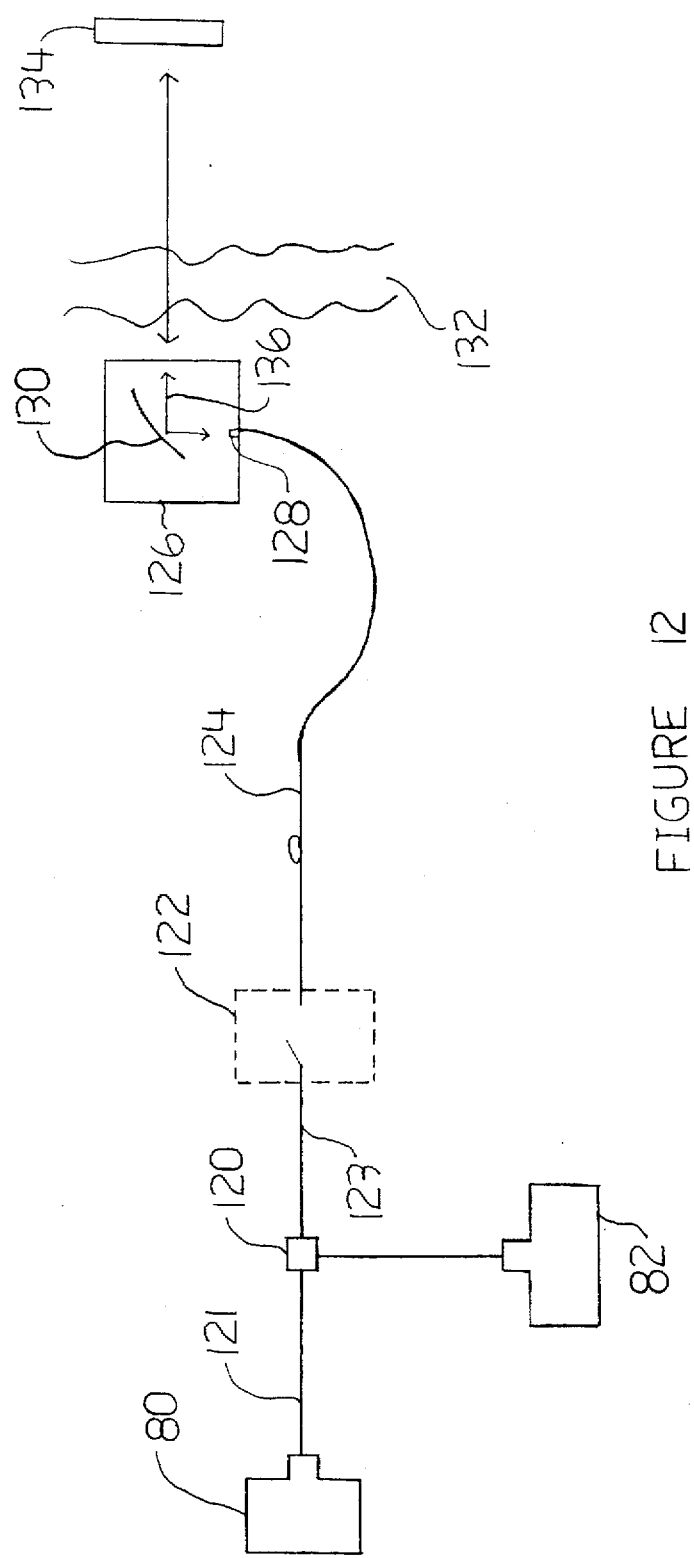
FIG. 12 is a schematic of an embodiment of the invention using a single fiber optic for outgoing and return light.

A further embodiment of the invention is shown in FIG. 12. A laser transmitter 80 is attached to one end of a guided light path extending to a target zone 132. The guided light path includes an optical fiber 121 connected to a directional coupler 120, an optical switch 122, a fiber 123 connecting optical coupler 120 and switch 122, a laser head 126, and an optical fiber 124 connecting switch 122 and laser head 126. Laser head 126 includes an end 128 of fiber optic 126 and a collimating parabolic offset mirror 130 oriented with the end 128 at the focus of the mirror. Mirror 130 acts both to collimate light exiting the fiber optic 124 and to collect light returning back from the reflector 134 at the opposite side of target zone 132 from the laser head 126. Various optical arrangements may be used with like effect. Mirror 130 is similar to mirror 98 only mirror 130 does not need to have a central aperture.

In the embodiment shown in FIG. 12, when switch 122 is closed to connect fibers 123 and 124, light from the laser transmitter 80 passes along fiber 121 through directional coupler 120 along fiber 123, through switch 122, along fiber 124 to laser head 126. Light from the end 128 of fiber 124 is collimated by mirror 130 and directed across the target zone to reflector 134. Light reflected back from the reflector 134 is collected and focused by mirror 130 back into fiber 124. With the switch 122 still closed, the light passes along fiber 123 and is directed by directional coupler 120 into laser receiver 82. In this manner only a single optic fiber is required for the guided light path out to the remote laser head. Only a single directional coupler 120 is required for several output/input optical fibers 124 if it is located on the laser transmitter side of switch 122. Numerous similar single fiber light paths may be connected through switch 122 in the same manner as with switch 100. The optical components described here are all conventional and readily commercially available.

With the remote laser head of the present invention, the laser transmitter and laser receiver may be located outside of a hazardous environment and thus do not need to be housed in an explosion proof housing. Likewise, the laser head may be simply constructed with no electrical connections in the hazardous area.

A person skilled in the art could make immaterial modifications to the invention described and claimed in this patent without departing from the essence of the invention.

The embodiments of the invention in which an exclusive property or privilege is claimed are defined as follows:

1. A gas detector for detecting gas in physically separate target zones, the gas detector comprising:
   a laser transmitter comprising a tunable laser diode;
   a laser receiver for receiving light transmitted by the laser transmitter after traversing a light path that includes one of the target zones, the laser receiver including means for producing output signals that are unaffected by variations in the length of the light path;
   a signal analyzer for analyzing output signals from the laser receiver to give an indication of whether gas is present in a target zone;
   plural single-mode optical light guides, each single-mode optical light guide being capable of forming a distinct guided light path between the laser transmitter and the laser receiver traversing one of the target zones; and
   single-mode optical switch means positioned between the laser transmitter and the single-mode optical light guides for selecting one of the single-mode optical light guides to complete a guided light path between the laser transmitter and the laser receiver for the detection of gas in the target zone traversed by the selected one of the single-mode optical light guides.

2. The gas detector of claim 1 in which each single-mode optical light guide includes a laser head remote from the laser transmitter and the laser receiver, and the laser head of each single-mode optical light guide comprises:
   optical means to direct collimated light through a target zone, collect light that has passed through a target zone and output the collected light to the laser receiver.

3. The gas detector of claim 2 in which each laser head is installed at a respective one of the target zones, and further comprising, for each laser head and for each target zone:
   a reflector spaced from the laser head, with the target zone between the reflector and the laser head, the reflector being disposed to reflect light back to the laser head.

4. The gas detector of claim 3 in which the laser head is connected to the laser transmitter through a first single-mode optical fiber and to the laser receiver through a second single-mode optical fiber and each optical means comprises:
   a collimating optic to focus light exiting the first single-mode optical fiber; and
   a collecting optic for directing light into the second single-mode optical fiber.

5. The gas detector of claim 3 further comprising:
   a controller operatively connected to the single-mode optical switch means for sequentially selecting one of the laser heads for gas detection.

6. The gas detector of claim 2 in which the laser head is connected to the laser transmitter through a first single-mode optical fiber and to the laser receiver through a second single-mode optical fiber and in which each optical means comprises:

a collimating optic to focus light exiting the first single-mode optical fiber; and a collecting optic for directing light into the second single-mode optical fiber.

7. The gas detector of claim 2 in which the laser head is coupled to the laser transmitter through a first single-mode optical fiber and further comprising:

a directional coupler mounted on the first single-mode optical fiber for directing light returning on the first single-mode optical fiber from the target zone to the laser receiver.

8. The gas detector of claim 2 further comprising:

a controller operatively connected to the single-mode optical switch means for sequentially selecting one of the laser heads for gas detection.

9. The gas detector of claim 1 further comprising:

a controller operatively connected to the single-mode optical switch means for sequentially selecting one of the optical light guides for gas detection.

* * * * *